US00PP26435P3

(12) United States Plant Patent
Keogh

(10) Patent No.: US PP26,435 P3
(45) Date of Patent: Mar. 1, 2016

(54) **VARIETY OF *TIBOUCHINA* NAMED 'PMA TIB 1'**

(50) Latin Name: *Tibouchina mutabalis*
Varietal Denomination: PMA Tib 1

(71) Applicant: Terry Keogh, Victoria Point (AU)

(72) Inventor: Terry Keogh, Victoria Point (AU)

( * ) Notice: Subject to any disclaimer, the term of this patent is extended or adjusted under 35 U.S.C. 154(b) by 178 days.

(21) Appl. No.: 13/815,685

(22) Filed: Mar. 14, 2013

(65) Prior Publication Data

US 2014/0283245 P1 Sep. 18, 2014

(51) Int. Cl.
*A01H 5/02* (2006.01)

(52) U.S. Cl.
USPC ..... Plt./226
CPC ..... *A01H 5/02* (2013.01)

(58) Field of Classification Search
USPC ..... Plt./226
See application file for complete search history.

(56) References Cited

PUBLICATIONS

Trademark "Illusion", Proven Winners North America LLC, serial No. 77639027, registration date May 4, 2010.*
UPOV hit for Tibouchina 'Illusion', application No. 2013125, filed May 27, 2013.*

* cited by examiner

*Primary Examiner* — Anne Grunberg
(74) *Attorney, Agent, or Firm* — The Webb Law Firm

(57) ABSTRACT

'PMA Tib 1' is a new variety of *Tibouchina* plant that is suitable for planting in gardens, containers, landscaping, and screen plantings having large flower size and volume that are mauve/purple at maturity.

3 Drawing Sheets

Botanical classification: *Tibouchina mutabalis.*
Varietal denomination: 'PMA TIB 1'.

BACKGROUND OF THE NEW PLANT

The present invention comprises a new and distinct cultivar of *Tibouchina* plant, botanically known as *Tibouchina mutabalis* and hereinafter referred to by the cultivar name 'PMA Tib 1'.

The new and ornamental variety was selected by the breeder as a result of an ongoing breeding program that has been conducted by the inventor for more than thirty years at the inventor's nursery in Victoria Point, Queensland, Australia. The purpose of the breeding program is to produce novel varieties of *Tibouchina* in varying plant sizes, flower colors, and which are well-suited to a range of climate zones. 'PMA Tib 1' is a hybrid plant derived from the deliberate controlled cross-pollination of the unpatented female parent, an individual seedling of *Tibouchina mutabilis,* named 'Noelene', and the unpatented male parent, an individual plant of *Tibouchina mutabilis* named 'Jazzie'. The inventor emasculated flowers of the female parent and applied pollen that was freshly collected from the male parent in 2002. The parent plants were isolated to prevent open pollination. In 2004, the inventor selected 'PMA Tib 1' as a seedling that had been raised from the cross-pollination described herein. Selection was based on the criteria of habit, flower color, and plant dimensions. The plant was then propagated in 2006 via vegetative cuttings to produce a new generation for final evaluation.

Further, asexual reproductions of 'PMA Tib 1' in Victoria Point, Queensland, Australia has demonstrated that the combination of characteristics as herein disclosed for the new cultivar are retained and reproduced true to type through more than six successive generations of asexual reproduction.

The color references made herein are to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'PMA Tib 1' which, in combination, distinguish this *Tibouchina* plant as a new and distinct cultivar:

1. White flowers with a purple margin upon first opening that turn completely mauve/purple when mature;
2. Dense plant habit;
3. Strong vigor;
4. Saucer-like, multi-colored flowers;
5. Large flower size with overlapping petals;
6. Abundant flowers; and
7. Woody, long-lived, and large shrub.

'Noelene' exhibits a lighter mauve/pink mature flower color, larger mature plant dimensions, and lack of significant petal overlap than 'PMA Tib 1'. 'Jazzie" exhibits smaller flowers than 'PMA Tib 1' and single purple colored petals that do not distinctly change in color.

Further, the new variety exhibits a larger flower size, larger mature plant dimensions, and significantly overlapping petals than 'Chameleon' (unpatented).

BRIEF DESCRIPTION OF THE DRAWINGS

The accompanying photographic drawings illustrate the new variety, with the colors being as nearly true as is possible with color illustrations of this type.

PROPAGATION

Figure 1:
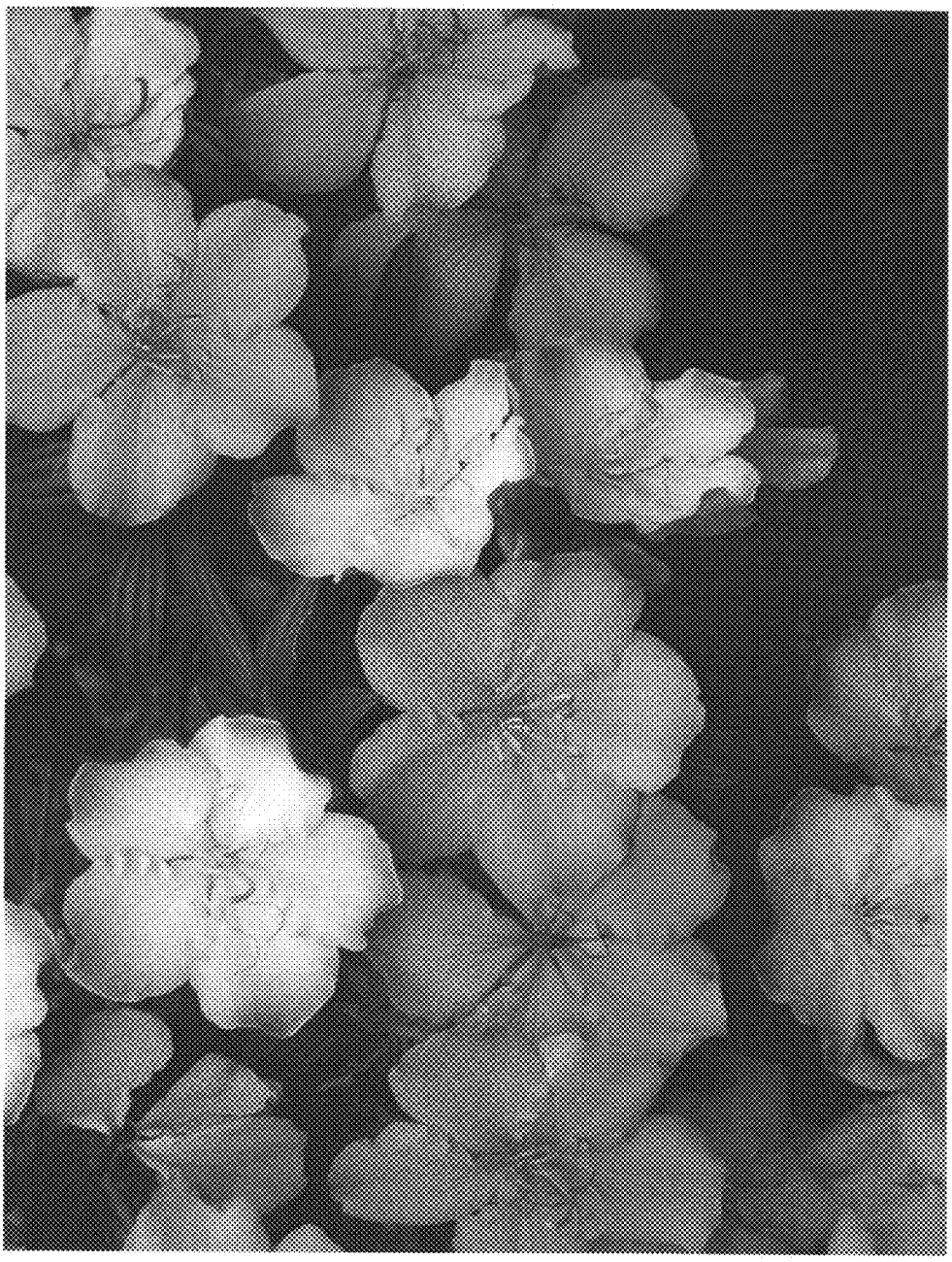
FIG. 1 is close-up photograph of flowers of the new variety.
Figure 2:
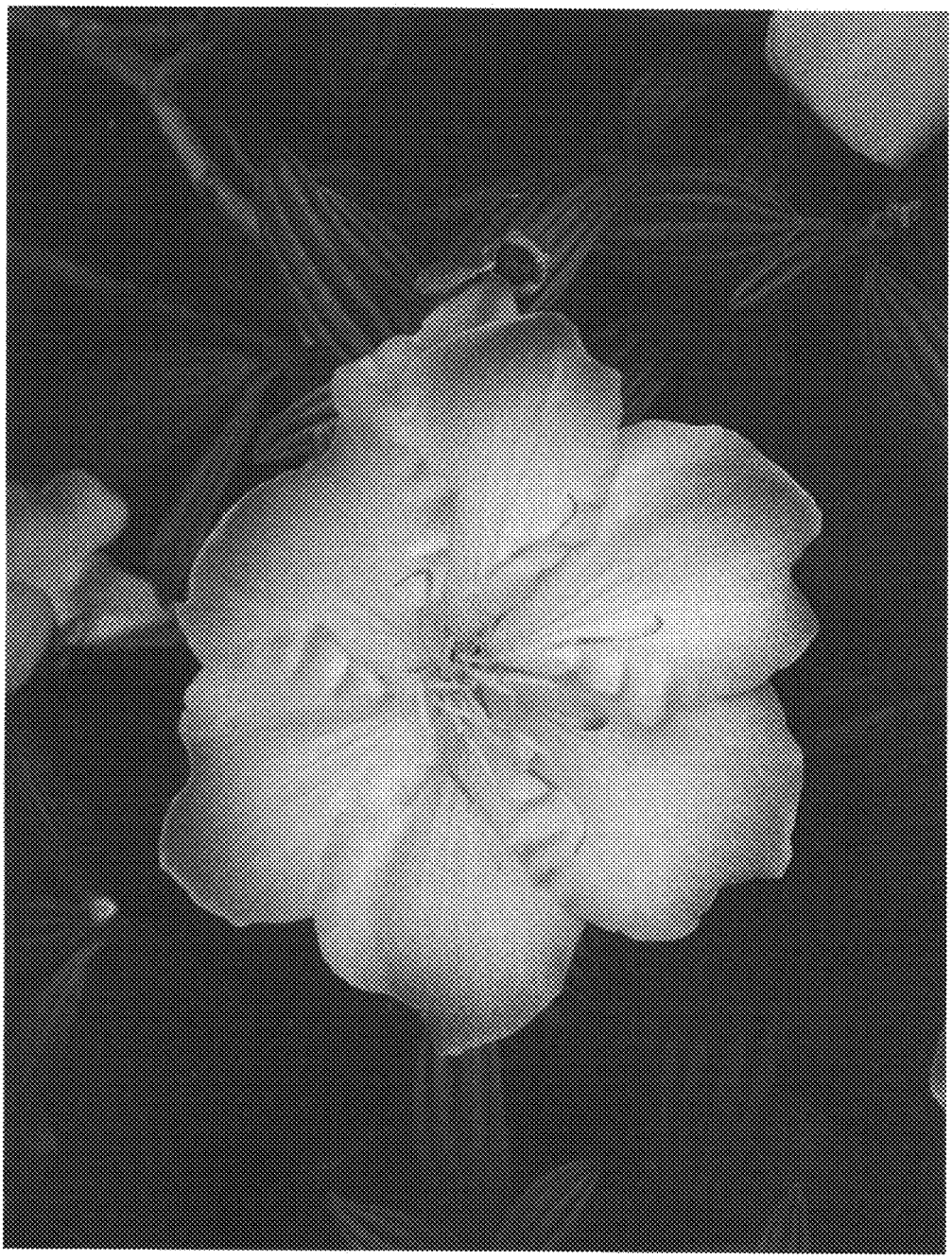
FIG. 2 is a close-up photograph of a flower of the new variety.
Figure 3:
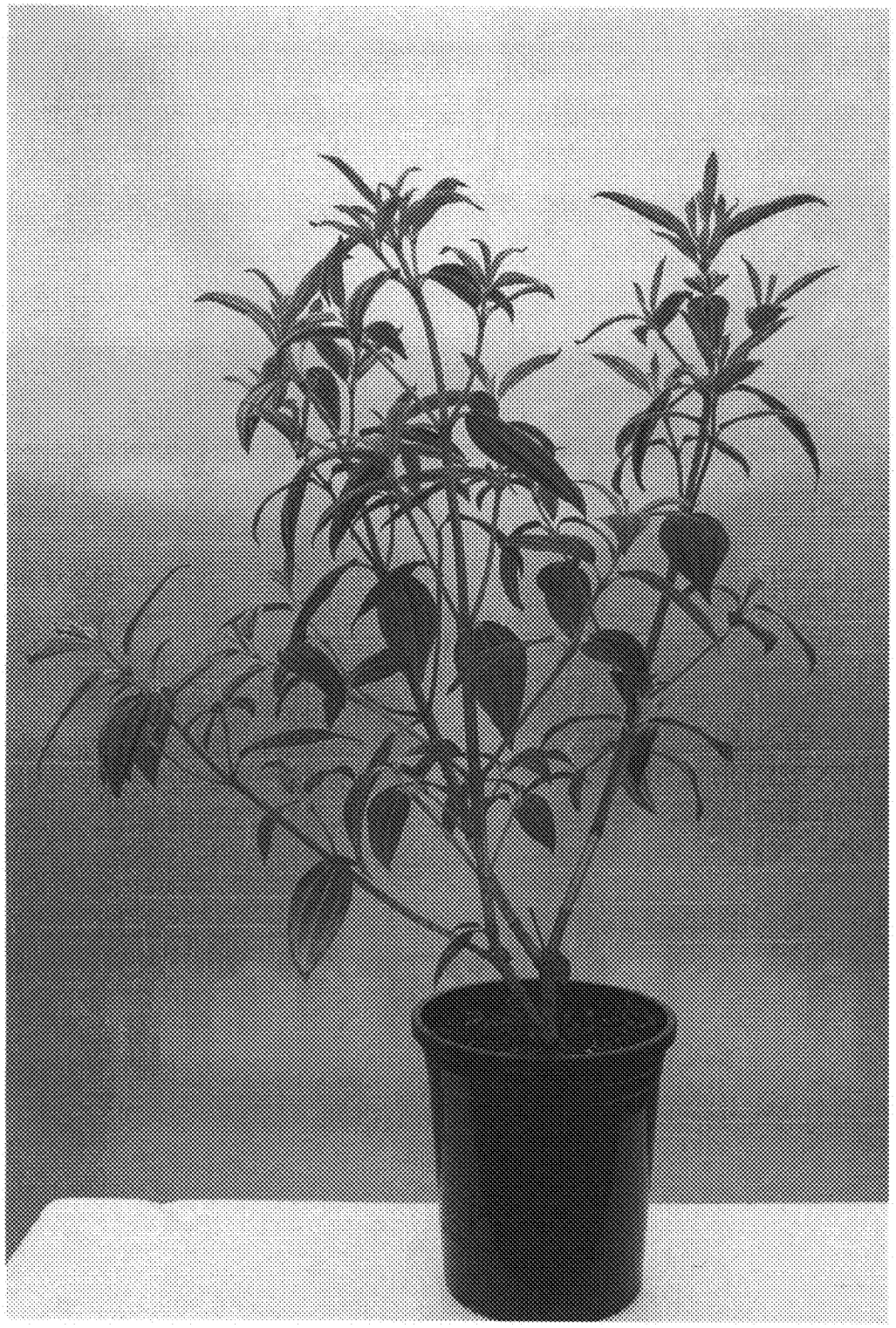
FIG. 3 is a photograph of an entire plant of the new variety.

*Time to initiate roots*.—About 14-18 days at approximately 21° C.

*Time to produce a rooted cutting*.—About 24-30 days at 21° C.

PLANT

*Plant spread*.—Approximately 27 cm.

*Plant height*.—50 cm.

*Growth rate*.—Fast.

*Lateral branches*.—Length: Approximately 37 cm. Diameter: Approximately 0.3 cm. Quantity: About 20.

*Age of plant when described*.—Approximately 16 weeks from a rooted cutting.

*Growth habit*.—Upright.

*Height at maturity*.—2.5 m.

*Width at maturity*.—2.5 m.

Stem:

*Branching habit*.—Very strong.

*Main stem diameter*.—0.85 cm.

*Lateral stem length* (*average*).—17 cm.

*Lateral stem width* (*average*).—0.3 cm.

*Internode length* (*range*).—2.0 cm to 10 cm.

*Shape*.—Square in cross section.

*Surface*.—Rough.

*Branch color*.—Juvenile: 146C. Semi-ripe: 176A and 146C. Mature: 199B.

Foliage:

*Leaf*.—Arrangement: Opposite. Division: Simple. Margin: Entire. Shape: Ovate. Base: Cuneate. Apex: Acute to acuminate. Surface (adaxial): Pubescent. Surface (abaxial): Pubescent. Texture (adaxial surface): Prominently ribbed. Texture (abaxial surface): Prominently ribbed. Attachment: Petiolate. Length (range excluding petiole): 2.5 cm to 10.5 cm. Width (range): 0.75 cm to 4.3 cm. Color (adaxial surface): 147A. Color (abaxial surface): 146B. Color of juvenile foliage not fully expanded: 171B to 171C and 147A.

*Foliar fragrance*.—None observed to date.

*Venation*.—Pattern: Reticulate; 3 to 5 primary parallel veins. Color (adaxial surface): 146B. Color (abaxial surface): 146D. Prominence (adaxial surface): Depressed. Vein prominence (abaxial surface): Raised.

*Petiole*.—Length (range): 0.7 cm to 2 cm. Diameter (average): 0.19 cm. Color: 146C and 174B. Surface: Pubescent. Shape: Cylindrical, but flattened on the adaxial surface.

Flower:

*Shape*.—Rotate.

*Aspect*.—Facing upward and outward.

*Inflorescence type*.—Solitary.

*Persistent or self-cleaning*.—Self-cleaning.

*Blooming period*.—Summer through fall; can bloom sporadically during other times.

*Inflorescence fragrance*.—None observed to date.

*Petals*.—Number: 5. Central color (both surfaces): 157D. Margin color (both surfaces): 39B. Central color as senesces: 65A. Margin: Entire and undulating. Apex: Obtuse. Base: Broadly attenuate. Petals overlapping: Present. Shape: Obovate. Surface (abaxial and adaxial): Glabrous. Fused or unfused: Unfused.

*Buds*.—Color: 80A. Shape: Elliptic. Apex: Acute.

*Calyx*.—Color: 47A. Shape: Cupule.

*Sepals*.—Color (adaxial surface): 135D. Color (abaxial surface): 175D. Quantity: 5 in number. Margin: Entire. Base: Truncate. Fused or unfused: Unfused.

*Peduncle*.—Color: 145B. Shape: Cylindrical.

Reproductive organs:

*Stamens*.—Number: Usually 10 in number (5 long and 5 short). Color at flower first opening: 155D. Color at flower senescence: 62D.

*Anthers*.—Color at flower first opening: 145A. Color at flower senescence: 76A. Shape: Sickle.

*Pollen*.—None observed.

*Pistil*.—Number: 1. Shape: Columnar and curved at the end. Color at flower first opening: 142B. Color at flower senescence: 186D.

*Stigma*.—Color: 157C. Shape: Flattened.

*Ovary*.—Color: 159A. Shape: Cupule. Position: Inferior.

*Seeds*.—No seeds have been observed to date.

I claim:

1. A new and distinct variety of *Tibouchina* plant named 'PMA Tib 1' as herein described and illustrated.

* * * * *